(12) United States Patent
Peng et al.

(10) Patent No.: US 8,168,683 B2
(45) Date of Patent: May 1, 2012

(54) FLUORINATED VINYLIDENE CATIONIC SURFACTANT

(75) Inventors: Sheng Peng, Hockessin, DE (US); Allison Mary Yake, Landenberg, PA (US); Cheryl Lynn Casper, Woolwich, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 386 days.

(21) Appl. No.: 12/579,515

(22) Filed: Oct. 15, 2009

(65) Prior Publication Data
US 2011/0092395 A1 Apr. 21, 2011

(51) Int. Cl.
| C07D 213/20 | (2006.01) |
| B01F 17/18 | (2006.01) |
| B01F 3/00 | (2006.01) |
| B01F 3/04 | (2006.01) |
| C09K 8/60 | (2006.01) |
| C09K 13/08 | (2006.01) |
| C08K 5/34 | (2006.01) |
| A62D 1/04 | (2006.01) |
| C09D 11/00 | (2006.01) |
| C11D 3/28 | (2006.01) |
| C08K 5/3432 | (2006.01) |

(52) U.S. Cl. ............ 516/201; 516/12; 516/26; 516/60; 546/346; 546/347; 507/130; 507/240; 507/242; 524/99; 524/462; 106/31.47; 106/506; 510/286; 510/500; 510/504

(58) Field of Classification Search .......... 546/346, 546/347; 516/12, 200, 201, 26, 60; 510/286, 510/500, 504; 252/3, 79.3; 507/130, 240, 507/242; 524/99, 462; 106/31.47, 506
See application file for complete search history.

(56) References Cited

U.S. PATENT DOCUMENTS

| 2,861,990 | A | * | 11/1958 | Cleaver et al. ............. 544/38 |
| 3,674,800 | A | * | 7/1972 | Sweeney et al. ............. 546/336 |
| 3,692,885 | A | * | 9/1972 | Anello et al. ............... 558/186 |
| 4,062,849 | A | * | 12/1977 | Foulletier et al. ........... 546/102 |
| 4,069,158 | A | * | 1/1978 | Bertocchio et al. ............. 252/3 |
| 4,107,055 | A | * | 8/1978 | Sukornick et al. ............ 442/94 |
| 4,183,367 | A | | 1/1980 | Goebel et al. |
| 4,351,946 | A | | 9/1982 | Toukan et al. |
| 4,420,434 | A | * | 12/1983 | Falk ........................... 562/105 |
| 4,459,221 | A | * | 7/1984 | Hisamoto et al. ............. 516/9 |
| 4,609,489 | A | * | 9/1986 | Hisamoto et al. ........... 516/201 |
| 4,672,118 | A | | 6/1987 | Fisk et al. |
| 4,729,849 | A | * | 3/1988 | Hisamoto et al. ........... 516/201 |
| 4,823,873 | A | | 4/1989 | Karydas |
| 4,836,281 | A | * | 6/1989 | Robin et al. ............... 166/270.1 |
| 4,836,958 | A | | 6/1989 | Karydas |
| 6,747,169 | B2 | | 6/2004 | Yanagi et al. |
| 2007/0029085 | A1 | | 2/2007 | Panga et al. |
| 2007/0225176 | A1 | | 9/2007 | Pope et al. |
| 2011/0092394 | A1* | | 4/2011 | Peng et al. .................. 507/102 |
| 2011/0092395 | A1* | | 4/2011 | Peng et al. .................. 507/105 |

FOREIGN PATENT DOCUMENTS
| GB | 1270838 | 4/1972 |
| JP | 61189268 | 8/1986 |

* cited by examiner

Primary Examiner — Daniel S Metzmaier

(57) ABSTRACT

A fluorinated pyridinium cationic compound of formula (I)

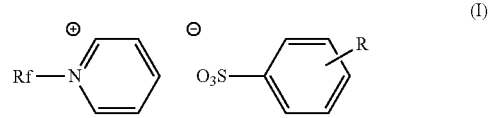

wherein,
Rf is $F(CF_2)_6(CH_2CF_2)_m(CH_2CH_2)_n-$,
m and n are each independently integers of 1 to 3, and
R is H, $C_1$ to $C_5$ linear or branched alkyl, or $C_1$ to $C_5$ linear or branched alkoxy, having surfactant properties for lowering surface tension in an aqueous medium or solvent medium, and for use as a foaming agent.

18 Claims, No Drawings

FLUORINATED VINYLIDENE CATIONIC SURFACTANT

FIELD OF THE INVENTION

This invention relates to a fluorinated pyridinium cationic surfactant for lowering surface tension in an aqueous medium or solvent medium and for use as a foaming agent.

BACKGROUND OF THE INVENTION

Fluorinated cationic compounds such as perfluoroalkyl quaternary ammonium derivatives are known in art, which have a saturated perfluoroalkyl terminal chain. For example, fluorinated cationic compounds disclosed in U.S. Pat. No. 4,836,958 contain such a perfluoroalkyl terminal chain group having up to 18 carbon atoms. In "Molecular Aggregation Structure and Surface Properties of Poly(fluoroalkylacrylate) Thin Films" Macromolecules (2005), 38(13), 5699-5705, Honda et al. describe that a perfluoroalkyl chain of at least 8 carbons is necessary for the individual perfluoroalkyl chains to be maintained in a parallel orientation. For such perfluoroalkyl chains containing fewer than 8 continuous perfluorinated carbons, a reorientation occurs, which decreases or even eliminates the performance of the materials in exhibiting desirable surface properties. Commercially available fluorinated pyridinium cationic surfactants usually contain a saturated perfluoroalkyl terminal chain of at least 8 or more carbons.

The high price of fluorinated surfactants is determined by the amount of fluorine incorporated therein. A higher fluorine content results in a higher price. Therefore, it is desirable to provide fluorinated surfactants having shorter fluorinated chains or less fluorine substitution in the chain while still providing equivalent or even better surface properties compared to those fluorinated surfactants which contain longer fully fluorinated perfluorinated chains.

It has been discovered in this invention that a fluorinated pyridinium cationic surfactant having a short partially fluorinated terminal chain provides desirable surface effects in a variety of applications, and is particularly useful in oil field and gas field applications.

SUMMARY OF THE INVENTION

The present invention comprises a compound of formula (I)

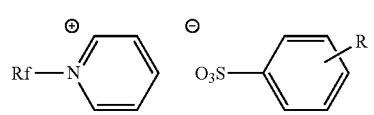

wherein,
Rf is $F(CF_2)_6(CH_2CF_2)_m(CH_2CH_2)_n-$,
m and n are each independently integers of 1 to 3, and
R is H, $C_1$ to $C_5$ linear or branched alkyl, or $C_1$ to $C_5$ linear or branched alkoxy.

The present invention further comprises a method of modifying surface effects of an aqueous medium or solvent medium comprising contacting the medium with a compound of formula (I) as described above.

DETAILED DESCRIPTION

As used herein, the term "surfactant" means surface-active agent, which refers to a substance which, even at low concentrations, effectively lowers the surface tension of a medium containing the surfactant by selective adsorption on the interface. A surfactant can be a pure chemical compound or a mixture of homologues or different chemical compounds.

The term "drill fluids" as used herein means those liquids that are added to a well or well bore penetrating a subterranean zone containing hydrocarbon or gas prior to or during a drilling operation. Examples can include water, brine, solvent, hydrocarbons, surfactants, oils, kerosene, fracturing fluids, stimulating fluids, oil-based drill muds, clay stabilizers, treatment fluids, and mixtures thereof.

The term "well fluids" as used herein means those liquids that occur in or are added to a well or well bore penetrating a subterranean zone containing hydrocarbon or gas. Examples can include drill fluids, water, brine, solvent, hydrocarbons, surfactants, oils, kerosene, fracturing fluids, stimulating fluids, oil-based drill muds, clay stabilizers, treatment fluids, and mixtures thereof.

The term "liquid treatment stream or gas treatment stream" as used herein means a liquid composition or gas composition, or a combination thereof, injected into a well penetrating a subterranean zone containing hydrocarbon or gas, or into a well bore area, in the operation of extracting the hydrocarbon or gas. Examples include steam, drill fluids, well fluids, water, brine, solvent, hydrocarbons, surfactants, fracturing fluids, stimulating fluids, oil-based drill muds, clay stabilizers, treatment fluids, and mixtures thereof.

The present invention comprises a fluorinated pyridinium cationic compound of the formula (I)

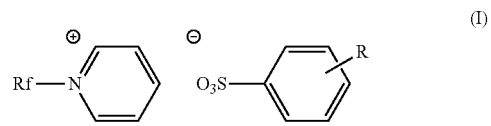

wherein,
Rf is $F(CF_2)_6(CH_2CF_2)_m(CH_2CH_2)_n-$,
m and n are each independently integers of 1 to 3, and
R is H, $C_1$ to $C_5$ linear or branched alkyl, or $C_1$ to $C_5$ linear or branched alkoxy.

Preferred compounds of formula (I) are those wherein m is 1 or 2, and n is 1 or 2. More preferred are those compounds of formula (I) wherein m is 1 or 2 and n is 1. Other preferred embodiments of formula (I) are those wherein R is hydrogen, methyl, ethyl, methoxy or ethoxy.

The compounds of formula (I) are prepared by the reaction of a pyridine with a fluorinated iodide followed by reaction of the resulting product with an arylsulfonic acid, typically in a solvent such as alcohol.

One example of such a preparation is detailed as follows. An intermediate iodide, such as compound $C_6F_{13}CH_2CF_2CH_2CH_2I$, is prepared by contacting $C_6F_{13}CH_2CF_2I$ with ethylene in the presence of d-(+)-limonene in an autoclave reactor at about 240° C. for about 12 hours. Then the resulting intermediate iodide, such as $C_6F_{13}CH_2CF_2CH_2CH_2I$, is contacted with pyridine, typically under an inert gas. The reaction is allowed to reflux at about 80° C. for several hours, typically about 20 hours. The reaction mixture is cooled and the product isolated and dried using known processes. The product of this example is $C_6F_{13}CH_2CF_2CH_2CH_2N^+(C_5H_5)$ $I^-$ which is then treated with alcohol under inert gas with heating to about 60° C. A solution of an arylsulfonic acid, such as p-toluenesulfonic acid in alcohol, is added drop wise into the reaction flask. The reaction is heated to about 60° C. for several hours, typically 75-80 hours, until $CH_3I$ can no longer be detected by gas chromatography in the distillate, while additional solvent is added periodically to replenish the distilled solvent. The product, $C_6F_{13}CH_2CF_2CH_2CH_2N^+C_6H_6$ $\rho\text{-}CH_3C_6H_4SO_3^-$, is isolated using standard techniques. In another embodiment of the invention, following the procedure above, the compound $C_6F_{13}CH_2CF_2CH_2CF_2CH_2CH_2I$ can be prepared by allowing $C_6F_{13}CH_2CF_2CH_2CF_2I$ to react with ethylene, which is then reacted to form $C_6F_{13}(CH_2CF_2)_2CH_2CH_2N^+ C_5H_5$ $\rho\text{-}CH_3C_6H_4SO_3^-$.

The surfactants comprising the fluorinated pyridinium cationic compounds of formula (I) are suitable for use in many applications, such as in coatings, oil/gas fields, fire fighting, polymerization, surface treatment and protection, agriculture, textiles, carpet, hard surface treatment and protections such as in flooring, stone and tiles, photovoltaic materials, and in automotive, herbicides, printing, paper and leather industries.

In one embodiment of the present invention the composition of the present invention is useful as a surfactant to affect surface tension or other surface properties of a medium or substrate. The compound of formula (I) is contacted with an aqueous medium or solvent medium. Examples of suitable media are selected from the group consisting of water, coating composition, latex, polymer, floor finish, fire fighting agent, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, and bonding agent. This embodiment is useful to affect the surface tension and other surface properties of the medium, or of a substrate to which the medium is applied. Types of surface behavior which can be altered using the compound of the present invention include, for example, wetting, penetration, spreading, leveling, flowing, emulsifying, dispersing, repelling, releasing, lubricating, etching, bonding, and stabilizing.

The above fluorinated pyridinium cationic compounds of formula (I) are suitable for use as surfactants to lower surface tension in a medium. The resulting surface tension values in a medium are less than about 25 milli-newtons per meter, preferably less than about 20 milli-newtons per meter, more preferably less than about 19 milli-newtons per meter at a concentration of the surfactant of less than about 0.5% by weight. Often such reduced surface tension is obtained at concentrations of less than about 0.2% by weight, or less than about 0.1% by weight. The surfactant is characterized by its efficiency in lowering the surface tension at low concentrations by selective adsorption on the interface determined by the amphiphilic nature of the surfactant. The term "amphiphilic" means attraction to two different kinds of media. Surfactants usually comprise a water-soluble hydrophilic part and a water-insoluble hydrophobic part.

The present invention further comprises a method of modifying surface effects of an aqueous medium or solvent medium comprising contacting the medium with a compound of formula (I) as defined above. One such surface effect is lowering surface tension of a medium by contacting the medium with the fluorinated pyridinium cationic compounds of formula (I). Examples of other surface behavior alteration include improvements in the properties of wetting, penetration, spreading, leveling, flowing, emulsifying, stabilization of dispersions in liquids, repellency, releasing, lubricating, etching, and bonding. Any of a wide variety of media is suitable for use in the method of the present invention. Typically the medium is an aqueous liquid or a solvent medium as detailed above.

Examples of such applications where low surface tension is required include coating compositions and aqueous and non-aqueous cleaning products, each for glass, wood, metal, brick, concrete, cement, natural and synthetic stone, tile, synthetic flooring, laminates, paper, textile materials, linoleum and other plastics, resins, natural and synthetic rubbers, fibers and fabrics, and paints; polymers; and waxes, finishes, leveling and gloss agents for floors, furniture, shoes, inks, and automotive care. Wetting agent applications include wetting agents for compositions containing herbicides, fungicides, weed killers, hormone growth regulators, parasiticides, insecticides, germicides, bactericides, nematocides, microbiocides, defoliants or fertilizers, therapeutic agents, antimicrobials, fluorochemical blood substitutes, textile treatment baths, and fiber spin finishes. Applications in personal care products include shampoos, conditioners, creme rinses, cosmetic products for the skin (such as therapeutic or protective creams and lotions, oil and water repellent cosmetic powders, deodorants and antiperspirants), nail polish, lipstick, and toothpaste. Further applications include fabric care products (such as stain pretreatments and/or stain removers for clothing, carpets and upholstery), and laundry detergents. Other applications include rinse-aids (for car washes and in automatic dishwashers), for oil well treatments (including drilling muds and additives to improve tertiary oil well recovery), extreme pressure lubricants, lubricating cutting oil to improve penetration times, writing inks, printing inks, photography developer solutions, emulsions for fighting forest fires, dry chemical fire extinguishing agents, aerosol-type fire extinguishers, thickening agents to form gels for solidifying or encapsulating medical waste, photoresists, developers, cleaning solutions, etching compositions, developers, polishers, and resist inks in the manufacturing, processing, and handling of semiconductors and electronics. The surfactants of formula (I) can be incorporated into products that function as antifogging agents for glass surfaces and photography films, and as antistatic agents for magnetic tapes, phonograph records, floppy disks, disk drives, rubber compositions, PVC, polyester film, and photography films, and as surface treatments for optical elements (such as glass, plastic, or ceramics). Other applications are in emulsifying agents, foaming agents, release agents, repellency agents, flow modifiers, film evaporation inhibitors, wetting agents, penetrating agents, cleaners, grinding agents, electroplating agents, corrosion inhibitors, soldering agents, dispersion aids, microbial agents, pulping aids, rinsing aids, polishing agents, drying agents, antistatic agents, antiblocking agents, bonding agents, and oil field chemicals.

Suitable medium include a coating composition, latex, polymer, floor finish, fire fighting agent, water, saline solution, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent.

In another embodiment of the present invention the compound of formula (I) of the present invention is useful in gas field and oil field applications. Herein a hydrocarbon is either a gas or oil product which is produced or recovered from a subterranean zone. A well or well bore is drilled and created to penetrate such a hydrocarbon-containing subterranean zone. The surfactant of the present invention is useful to modify and improve the wettability and surface conditions, such as the surface tension of the subterranean formation around the well bore, and is also useful to improve the permeability and flow rate to enhance oil well or gas well recovery and productivity.

The compound of formula (I) acts as a surfactant or foaming fluid. For gas and oil filed applications the compound of formula (I) is typically used in an aqueous medium selected from the group consisting of water, saline solution, KCl solution, HCl solution, hydrocarbon, halocarbon, drill fluids, well fluids, stimulation fluids, liquid treatment stream, gas treatment stream, and a mixture thereof. As a surfactant the composition is used as an additive in drill fluids, well fluids, and other treatment fluids for subterranean formations, to enhance gas or oil recovery by altering surface tension, wettability, or viscosity of the fluids, oils, condensates, and muds employed or encountered in such operations. The surfactant can be used for foaming porous rock or soil medium of a subterranean formation, or for other known well or well bore treatments.

The compound of the present invention provides a surfactant or foaming fluid which comprises the fluorinated pyridinium cationic compounds of formula (I) and a medium, wherein the fluorinated pyridinium cationic compounds of formula (I) is at a concentration range of from about 0.001% to about 50% by weight, preferably a range of from about 0.01% to about 30% by weight, and more preferably a range of from about 0.05% to about 20% by weight.

The present invention further comprises a method of foaming a well fluid to be introduced into a well bore penetrating a hydrocarbon-containing subterranean zone comprising the steps of 1) providing a composition of formula (I) of the present invention, and 2) contacting the composition with compressed air or a compressed inert gas to generate a foamed fluid.

The present invention further comprises a method of lowering the surface tension within a subterranean formation containing hydrocarbons comprising adding a compound of formula (I) as described above to a medium which is a carrier contacted with the subterranean formation. One method of contacting is injection of the carrier or medium containing a compound of the present invention into the subterranean formation, for example through a downhole, well, or well bore. The compound of formula (I) is added to a carrier or medium such as a fluid or gas which will be in contact with the subterranean formation during operations to remove oil or gas from the formation. Examples include drill fluids, well fluids, stimulation fluids, liquid treatment streams, gas treatment streams, fractionating fluids, clay stabilizers, or other liquids or gases employed when extracting the hydrocarbons from the formation. The compound of the present invention can be used in one or more carriers or media employed in a pretreatment stage of injection of a pre-flush of various liquids, or in matrix or stimulation activities; in the main stage in various carrier fluids, or in a soaking of the formation for a specific time period; or in a post treatment stage for displacement operation to achieve better placement of the fluids containing the surfactant composition. The compound of the present invention is used in the form of a liquid, emulsion, dispersion, or foaming agent.

Foaming is a desirable property of the surfactants of the present invention which are used as additives to drill fluids, well fluids, stimulation fluids, and other fluids in oil and/or gas field applications for enhanced production and recovery. The aqueous or solvent based drilling fluids, well fluids, stimulation fluids, and liquid or gas treatment streams, or other carriers or media which contain the compound of the present invention foam during drilling or well treatment processes, and therefore provide advantages for enhanced production and recovery. An example of such advantages from the surfactant and foaming properties include aiding in the removal of fines from the well around the drill-bit and wellbore treatment area, and adjusting the permeability and wettability properties where the fluids contact around the drill-bit and wellbore treatment area. The addition of the surfactant of the present invention boosts the foaming properties of the oil/gas well drilling fluids and treatment fluids. If these fines are not efficiently removed, they can result in damage to the drill-bit head, costing time and money to replace or repair. In addition the surfactant of the present invention is useful to reduce the viscosity of the hydrocarbon to permit easier extraction.

Another advantage of contacting a subterranean formation containing hydrocarbons with a fluorinated pyridinium cationic surfactant of the present invention as defined above is providing a method for stimulating production of hydrocarbons during operations to extract hydrocarbons from a subterranean formation. The fluorosurfactant compounds of the present invention are useful as stimulation fluid additives for stimulation activities, such as hydraulic fracturing and acidizing. In these situations the stable foams of the present invention improve the wetting of the stimulation fluid on the formation surface (rock) to allow for deeper penetration and better stimulation of the well bore region. The low surface tension of these additives permits the stimulation fluids to be more efficiently and easily recovered from downhole. As a result, the well will be able to more effectively produce gas and oil.

The surfactant compound of the present invention is further useful as an aid to prevent and remedy water blocks or condensate blocks in wells or well bore areas. It is known that water can accumulate near the well bore of an oil or gas well and decrease productivity by decreasing the relative permeability of the oil or gas, which is called water block. In addition liquid hydrocarbons can also accumulate and cause a decrease in productivity in gas wells near or far from the well bore region known as condensate block. The compounds of the present invention can be used to help in removal of at least a portion of such accumulations of liquids in a water block or condensate block, or for reducing or preventing the formation of the accumulation of liquids in such blocks. The fluorinated pyridinium cationic surfactant of the present invention is particularly useful as a surfactant additive in drill fluids, well fluids and treatment fluids for subterranean formations to alter the wettability and permeability of the formation by its surface active properties or by generating foams. The surfactants, for example, are used within the porous rock medium of subterranean formation and can result in pressure changes or as foams can block the gas drain paths and result in the oil/gas recovery increases.

The compound of the present invention provides advantages in that desirable surface effects are obtained using a surfactant containing a partially fluorinated perfluoroalkyl chain having a short (six continuous carbons) terminal fully fluorinated group. Thus the compositions of the present invention are more economical than surfactants containing longer chain perfluoroalkyls or mixtures of homologues of perfluoroalkyls, while providing comparable or superior performance.

Materials and Test Methods

The following materials and test methods were used in the Examples herein.

Compound 1—$C_6F_{13}CH_2CF_2CH_2CH_2I$

Ethylene (15 g, 0.53 mol) was introduced to an autoclave charged with $C_6F_{13}CH_2CF_2I$ (170 g, 0.33 mol) and d-(+)-limonene (1 g), and then the reactor was heated at 240° C. for 12 hours. Product $C_6F_{13}CH_2CF_2CH_2CH_2I$ was obtained via vacuum distillation in 68% yield (b.p. 102~105° C. at 2666 pascal).

Compound 2—$C_6F_{13}CH_2CF_2CH_2CF_2CH_2CH_2I$

Ethylene (56 g, 2.0 mol) was introduced to an autoclave charged with $C_6F_{13}(CH_2CF_2)_2I$ (714 g, 1.24 mol) and d-(+)-limonene (3.2 g), and then the reactor was heated at 240° C. for 12 hours. Product $C_6F_{13}CH_2CF_2CH_2CF_2CH_2CH_2I$ was obtained via vacuum distillation in 84% yield (b.p. 124~128° C. at 1600 pascal).

Test Method 1—Surface Tension Measurement

A stock solution was prepared for the highest concentration of fluorosurfactant to be analyzed. The concentration of the solutions was by percent active ingredient, weight percent or fluorine content. This stock solution was prepared in deionized water, 2% KCl water, or 15% HCl water depending on the desired oilfield application for which the surface tension was being measured. The stock solution was stirred overnight (for approximately 12 hours) to ensure complete mixing. Additional concentrations of the fluorosurfactant for analysis were made by diluting the stock solution according to the equation $M_iV_i=M_fV_f$, where $M_i$ is the concentration of the stock solution, $M_f$ is the concentration of the final solution, $V_f$ is the final volume of the sample, and $V_i$ is the volume of the stock solution that is needed in order to formulate the final sample. The concentration dilution samples were shaken thoroughly and then left to sit undisturbed for 30 minutes. These samples were then mixed and poured into a small container. Solutions of 2% KCl and 15% HCl were typically used in the surface tension measurements for oilfield applications because they mimic the stimulation fluid types that are pumped down hole into wells. The 2% KCl solution was similar to the salinity of the fracture fluids that are used to hydraulically fracture a well. The 15% HCl solution emulated the acidizing stimulation treatment fluid that is used to help dissolve the formation rock in wells. The surface tension was measured using a Kruess Tensiometer, K11 Version 2.501 in accordance with instructions with the equipment. The Wilhelmy Plate method was used. A vertical plate of known perimeter was attached to a balance, and the force due to wetting was measured. 10 replicates were tested of each dilution, and the following machine settings were used:

Method: Plate Method SFT
Interval: 1.0 s
Wetted length: 40.2 mm
Reading limit: 10
Min Standard Deviation: 2 dynes/cm
Gr. Acc.: 9.80665 m/s^2

Lower surface tension indicated superior performance.

Test Method 2—Foaming

The test procedure used to evaluate the foaming of fluorosurfactants for oilfield applications was a nitrogen bubble foaming test. First, stock solutions of the testing base solutions were made. These solutions were deionized water, 2% KCl, and 15% HCl. Samples of 20 mL of the fluorosurfactant at 0.1% active ingredient in the desired base testing solution were prepared and stirred overnight to ensure complete mixing. The sample solution was then added to a 100 mL graduated cylinder (glass). Nitrogen was then bubbled through the solution to produce foam at a rate that filled the cylinder in 20-30 seconds. A fritted glass tube was used to bubble the nitrogen through the solution. When the foam reached the top of the cylinder, the nitrogen was turned off and a timer was started. The heights of the foam and liquid in mL were measured after 30 seconds, 5 minutes, 10 minutes, and 15 minutes. A difference in foam height of up to 10 mL was within the variation of this method. Observations of the quality and persistency of the foam were also recorded. At least three repetitions were conducted for each sample test. This nitrogen bubbling foam test was used as an indicator of the amount of foam that a sample produced and the persistency of that foam. Higher foam heights which lasted for a longer time indicated superior performance.

EXAMPLES

Example 1

A 100 mL, three-neck roundbottom flask was charged with $C_6F_{13}CH_2CF_2CH_2CH_2I$ (20.0 g, 0.0372 mol) and pyridine (18.6 g, 0.235 mol) under nitrogen. The reaction was allowed to reflux at 80° C. for 20 hours. The reaction mixture was cooled to room temperature before isolating the off-white solid product (21.44 g, 93%) in a fritted funnel. The product was washed with ethyl acetate (3×60 mL), and dried under vacuum overnight. The product, $C_6F_{13}CH_2CF_2CH_2CH_2N^+(C_5H_5)$ $I^-$, was characterized as:

m.p.: 188-193° C.

$^1$H NMR (DMSO-$d_6$, 400 MHz) δ 9.17 (2H, d, J=6.2 Hz), 8.65 (1H, t-t, J1=7.8 Hz, J2=1.3 Hz), 8.21 (2H, t, J=7.0 Hz), 4.92 (2H, t, J=7.2 Hz), 3.47~3.28 (2H, m), 2.50 (2H, t-t, J1=17.7 Hz, J2=6.9 Hz)

$^{19}$F NMR (DMSO-$d_6$, 376 MHz) δ −80.67 (3F, t, J=9.8 Hz), −95.38~−95.59 (2F, m), −111.58~−111.80 (2F, m), −121.86~−122.10 (2F, m), −122.90~−123.14 (2F, s), −123.19~−123.40 (2F, m), −126.05~−126.24 (2F, m)

A 100 mL, three-neck roundbottom flask equipped with a distillation column was charged with $C_6F_{13}CH_2CF_2CH_2CH_2N^+(C_5H_5)I^-$ (10.0 g, 0.016 mol) and methanol (6.8 g, 0.21 mol) under nitrogen and heated to 60° C. A solution of p-toluenesulfonic acid (3.61 g, 0.019 mol) in methanol (3.4 g, 0.107 mol) was added drop wise into the reaction flask. The reaction was heated to 60° C. for 79 hours (when $CH_3I$ could no longer be detected by GC in the distillate), while additional methanol was added periodically to replenish the distilled solvent. Methanol was then evaporated off to yield the product as a light yellow powder (10.71 g, 100%). The product, $C_6F_{13}CH_2CF_2CH_2CH_2N^+C_5H_5$ $\rho$-$CH_3C_6H_4SO_3$, was then dissolved in methanol to obtain a 50% solution, and neutralized to a pH of 5.5±0.5 with 3.5% NaOH aqueous solution. The product was tested for surface tension and foaming using Test Methods 1 and 2. Results are in Tables 1 to 6.

Example 2

A 100 mL, three-neck roundbottom flask was charged with $C_6F_{13}(CH_2CF_2)_2CH_2CH_2I$ (20.0 g, 0.0332 mol) and pyridine (17.4 g, 0.210 mol) under nitrogen. The reaction was allowed to reflux at 80° C. for 20 hours. The reaction mixture was then cooled to room temperature before isolating the off-white solid product (20.32 g, 90%) in a fritted funnel. The product was washed with ethyl acetate (3×60 mL), and dried under vacuum overnight. The product, $C_6F_{13}(CH_2CF_2)_2CH_2CH_2N^+(C_5H_5)$ I, was characterized as:

m.p.: 138~145° C.

$^1$H NMR (CDCl$_3$, 400 MHz) δ 9.49 (2H, d, J=5.8 Hz), 8.50 (1H, t-t, J1=7.7 Hz), 8.09 (2H, t, J=7.1 Hz), 4.93 (2H, t, J=6.3 Hz), 3.03 (2H, t-t, J1=17.6 Hz, J2=6.5 Hz), 2.95~2.76 (4H, m)
$^{19}$F NMR (CDCl$_3$, 376 MHz) δ −81.19 (3F, t-t, J1=9.9 Hz, J2=2.2), −89.83~−90.04 (2F, m), −94.10~−94.30 (2F, m), −112.54~−112.74 (2F, m), −121.96~−122.18 (2F, m), −123.09~−123.27 (2F, m), −123.65~−123.81 (2F, m), −126.41~−126.54 (2F, m)

A 100 mL, three-neck roundbottom flask equipped with a distillation column was charged with C$_6$F$_{13}$(CH$_2$CF$_2$)$_2$CH$_2$CH$_2$N$^+$(C$_5$H$_5$)I$^-$ (10.0 g, 0.015 mol) and methanol (6.1 g, 0.19 mol) under nitrogen and heated to 60° C. A solution of p-toluenesulfonic acid (3.3 g, 0.017 mol) in methanol (3.1 g, 0.097 mol) was added drop wise into the reaction flask. The reaction was heated to 60° C. for 98 hours (when CH$_3$I could no longer be detected by GC in the distillate), while additional methanol was added periodically to replenish the distilled solvent. Methanol was then evaporated off to yield the product as a light yellow gum (10.64 g, 100%). The product, C$_6$F$_{13}$(CH$_2$CF$_2$)$_2$CH$_2$CH$_2$N$^+$(C$_5$H$_5$) ρ-CH$_3$C$_6$H$_4$SO$_3^-$, was then dissolved in methanol to obtain a 50% solution, and neutralized to a pH of 5.5±0.5 with 3.5% NaOH aqueous solution. The product was tested for surface tension and foaming using Test Methods 1 and 2. Results are in Tables 1 to 6.

Example 3

Example 3 was prepared by mixing the products of Examples 1 and 2. Example 3 was a mixture of 90% C$_6$F$_{13}$CH$_2$CF$_2$CH$_2$CH$_2$N$^+$C$_5$H$_5$ ρ-CH$_3$C$_6$H$_4$SO$_3^-$ and 10% C$_6$F$_{13}$(CH$_2$CF$_2$)$_2$CH$_2$CH$_2$N$^+$(C$_5$H$_5$) ρ-CH$_3$C$_6$H$_4$SO$_3^-$. The product was tested for surface tension and foaming using Test Methods 1 and 2. Results are in Tables 1 to 6.

Example 4

Example 4 was prepared by mixing the products of Examples 1 and 2. Example 4 was a mixture of 80% C$_6$F$_{13}$CH$_2$CF$_2$CH$_2$CH$_2$N$^+$C$_5$H$_5$ ρ-CH$_3$C$_6$H$_4$SO$_3^-$ and 20% C$_6$F$_{13}$(CH$_2$CF$_2$)$_2$CH$_2$CH$_2$N$^+$(C$_5$H$_5$) ρ-CH$_3$C$_6$H$_4$SO$_3^-$. The product was tested for surface tension and foaming using Test Methods 1 and 2. Results are in Tables 1 to 6.

Comparative Example A

The process of Example 1 was employed using the formula C$_8$F$_{17}$CH$_2$CH$_2$I as a starting material. The resulting product C$_8$F$_{17}$CH$_2$CH$_2$N$^+$(C$_5$H$_5$) ρ-CH$_3$C$_6$H$_4$SO$_3^-$ was tested for surface tension and foaming using Test Methods 1 and 2. Results are in Tables 1 to 6.

Comparative Example B

The process of Example 1 was employed using the formula C$_6$F$_{17}$CH$_2$CH$_2$I as a starting material. The resulting product C$_6$F$_{17}$CH$_2$CH$_2$N$^+$(C$_5$H$_5$) ρ-CH$_3$C$_6$H$_4$SO$_3^-$ was tested for surface tension and foaming using Test Methods 1 and 2. Results are in Tables 1 to 6.

TABLE 1

Surface Tension in Deionized Water (dynes/cm)

| Example* | 0% | 0.001% | 0.01% | 0.1% | 0.5% |
|---|---|---|---|---|---|
| 1 | 72.9 | 69.5 | 45.6 | 18.3 | 17.2 |
| 2 | 72.8 | 64.2 | 34.7 | 18.8 | 18.3 |
| 3 | 72.8 | 68.9 | 43.0 | 18.1 | 17.5 |
| 4 | 72.7 | 67.8 | 40.6 | 18.2 | 17.6 |
| Comparative A | 72.8 | 60.9 | 30.6 | 17.2 | 17.0 |
| Comparative B | 72.7 | 72.2 | 59.3 | 26.5 | 16.9 |

*Example was added to deionized water by weight based on solids of the additive in methanol.
*Standard Deviation <1 dynes/cm
*Temperature 23° C.

TABLE 2

Surface Tension in 2% KCl Aqueous Solution (dynes/cm)

| Example* | 0% | 0.001% | 0.01% | 0.1% | 0.5% |
|---|---|---|---|---|---|
| 1 | 74.3 | 54.5 | 32.2 | 18.6 | 17.5 |
| 2 | 74.2 | 42.3 | 19.4 | 18.2 | 17.6 |
| 3 | 74.5 | 53.7 | 28.2 | 18.3 | 17.4 |
| 4 | 74.3 | 52.8 | 25.4 | 18.4 | 17.7 |
| Comparative A | 74.2 | 68.5 | 57.4 | 40.0 | 21.8 |
| Comparative B | 74.3 | 65.9 | 51.4 | 27.5 | 18.8 |

*Example was added to 2% KCl aqueous solution by weight based on solids of the additive in methanol
*Standard Deviation <1 dynes/cm
*Temperature 23° C.

TABLE 3

Surface Tension in 15% HCl Aqueous Solution (dynes/cm)

| Example* | 0% | 0.001% | 0.01% | 0.1% | 0.5% |
|---|---|---|---|---|---|
| 1 | 72.5 | 51.7 | 29.9 | 20.0 | 19.0 |
| 2 | 72.7 | 41.7 | 19.1 | 18.6 | 18.6 |
| 3 | 72.8 | 51.5 | 26.0 | 19.7 | 18.9 |
| 4 | 72.9 | 50.5 | 24.4 | 19.6 | 18.8 |
| Comparative A | 72.5 | 37.9 | 19.2 | 19.2 | 18.4 |
| Comparative B | 72.8 | 63.7 | 47.8 | 26.8 | 22.8 |

*Example was added to 15% HCl aqueous solution by weight based on solids of the additive in methanol
*Standard Deviation <1 dynes/cm
*Temperature 23° C.

Normal surface tension of deionized water, 2% KCl aqueous solution and 15% HCl aqueous solution is about 72 dyne/cm (shown in Tables 1 to 3 as 0.000%). When the surfactant of the present invention was added at a specified rate, the surface tension of each aqueous solution was reduced significantly. Better performance was obtained at higher levels. According to the results from the test, excellent surface tension reduction was seen using Examples 1 to 4 of the present invention. All of Examples 1 to 4 were equal to or comparable to the Comparative Example A (containing 8 continuous fully fluorinated perfluoroalkyl carbons) at the higher concentrations tested. All of Examples 1 to 4 were superior in performance to Comparative Example B (containing 6 continuous fully fluorinated perfluoroalkyl carbons). Thus Examples 1 to 4 having a perfluoroalkyl interrupted by a CH$_2$ group provided better performance versus Comparative Example B.

TABLE 4

Foaming in Deionized Water

| | Foam Volume (mL) | | | | |
|---|---|---|---|---|---|
| Example* | Initial | t = 30 sec | t = 5 min | t = 10 min | t = 15 min |
| 1 | 100 | 93 | 87 | 77 | 75 |
| 2 | 106 | 105 | 97 | 91 | 73 |
| 3 | 103 | 98 | 84 | 74 | 68 |
| 4 | 105 | 97 | 88 | 73 | 65 |
| Comparative A | 106 | 100 | 97 | 86 | 73 |
| Comparative B | 98.3 | 13.3 | 6.7 | 1.7 | 0.0 |

*Example was added to deionized water by weight based on solids of the additive in methanol to make 100 mL 0.1% solution

TABLE 5

Foaming in 2% KCl Aqueous Solution

| | Foam Volume (mL) | | | | |
|---|---|---|---|---|---|
| Example* | Initial | t = 30 sec | t = 5 min | t = 10 min | t = 15 min |
| 1 | 110 | 101 | 99 | 88 | 75 |
| 2 | 106 | 101 | 91 | 71 | 66 |
| 3 | 110 | 102 | 99 | 89 | 78 |
| 4 | 113 | 105 | 101 | 89 | 78 |
| Comparative A | 111 | 101 | 101 | 81 | 76 |
| Comparative B | 104.3 | 44.3 | 4.3 | 3.3 | 3.0 |

*Example was added to 2% KCl aqueous solution by weight based on solids of the additive in methanol to make 100 mL 0.1% solution

TABLE 6

Foaming in 15% HCl Aqueous Solution

| | Foam Volume (mL) | | | | |
|---|---|---|---|---|---|
| Example* | Initial | t = 30 sec | t = 5 min | t = 10 min | t = 15 min |
| 1 | 116 | 105 | 101 | 99 | 99 |
| 2 | 117 | 107 | 106 | 106 | 106 |
| 3 | 114 | 108 | 106 | 106 | 106 |
| 4 | 108 | 102 | 101 | 101 | 101 |
| Comparative A | 116 | 106 | 106 | 106 | 106 |
| Comparative B | 118 | 102.7 | 47.7 | 41.5 | 19.3 |

*Example was added to 15% HCl aqueous solution by weight based on solids of the additive in methanol to make 100 mL 0.1% solution All Examples 1 to 4 of the present invention generally showed comparable performance to the Comparative Example A (containing 8 continuous fully fluorinated carbons). Examples 1 to 4 demonstrated superior performance versus Comparative Example B. Comparative Example B (containing 6 continuous fully fluorinated carbons) did not maintain foam height over time. This data demonstrated that Examples 1 to 4 wherein the perfluoroalkyl group is interrupted by a $CH_2$ group provided superior performance to Comparative Example B lacking this interruption.

What is claimed is:

1. A compound of formula (I)

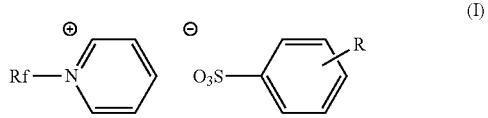

(I)

wherein
Rf is $F(CF_2)_6(CH_2CF_2)_m$—$(CH_2CH_2)_n$—,
m and n are each independently integers of 1 to 3, and
R is H, $C_1$ to $C_5$ linear or branched alkyl, or $C_1$ to $C_5$ linear or branched alkoxy.

2. The compound of claim 1 wherein m is 1 or 2 and n is 1.

3. The compound of claim 1 having a surface tension of about 25 mN/m or less at a concentration of 0.1% by weight in aqueous solution.

4. The compound of claim 1 having a surface tension of about 20 mN/m or less at a concentration of 0.1% by weight in aqueous solution.

5. A composition comprising:
a liquid or solvent selected from the group consisting of water, saline solution, KCl solution, HCl solution, hydrocarbon, halocarbon, drill fluid, well fluid, liquid treatment stream for subterranean formations and gas treatment stream for subterranean formations, and
the compound according to claim 1.

6. The composition of claim 5 wherein the compound of formula (I) is present at a concentration range of from 0.001% to 50% by weight.

7. The composition of claim 5 wherein said compound is present at a concentration range of from 0.01% to 30% by weight.

8. A composition in the form of a foam comprising the compound according to claim 1.

9. A method of modifying a surface effect of an aqueous medium or solvent medium comprising contacting the medium with a compound of formula (I)

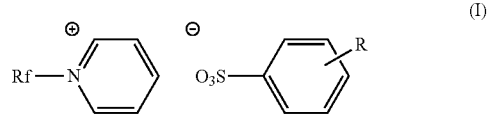

(I)

wherein
Rf is $F(CF_2)_6(CH_2CF_2)_m$—$(CH_2CH_2)_n$—,
m and n are each independently integers of 1 to 3, and
R is H, $C_1$ to $C_5$ linear or branched alkyl, or $C_1$ to $C_5$ linear or branched alkoxy.

10. The method of claim 9 wherein the medium is selected from the group consisting of water, saline solution, KCl solution, HCl solution, drill fluids, well fluids, liquid treatment for subterranean formation stream, gas treatment stream for subterranean formation, liquid treatment stream for well bore areas, gas treatment stream for well bore areas, hydrocarbon, halocarbon system, coating composition, latex, polymer, floor finish, floor polish, fire fighting agent, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, and bonding agent.

11. The method of claim 9 wherein the surface effect is lowering the surface tension.

12. The method of claim 9 wherein the surface effect is selected from the group consisting of wetting, penetration, spreading, leveling, flowing, emulsifying, dispersing, repelling, releasing, lubricating, etching, bonding, and stabilizing.

13. The method of claim 9 wherein the compound of formula (I) is added to a medium to be contacted with a hydrocarbon-bearing subterranean formation.

14. The method of claim 13 wherein the medium is a fluid injected into the subterranean formation.

15. The method of claim 13 wherein the medium is selected from the group consisting of water, saline solution, KCI solution, HCI solution, hydrocarbons, halocarbons, drill fluids, well fluids, stimulating fluids, liquid treatment stream for subterranean formation, gas treatment stream for subterranean formation, liquid treatment stream for well bore areas and gas treatment stream for well bore areas.

16. The method of claim 13 wherein the compound of formula (I) is present in the medium at a concentration of from about 0.001% to about 50% by weight.

17. The method of claim 13 wherein the medium containing the compound of formula (I) is to be contacted with the subterranean formation during an operation to remove hydrocarbons from the formation for stimulating production of such removal.

18. The method of claim 13 wherein the medium containing the compound of formula (I) is to be contacted with the subterranean formation during an operation to prevent or remedy water blocks or condensate blocks.

* * * * *